(12) United States Patent
Sung et al.

(10) Patent No.: US 10,322,088 B2
(45) Date of Patent: Jun. 18, 2019

(54) SUSTAINED-RELEASE COMPOSITION, METHOD FOR FABRICATING, AND USE THEREOF

(71) Applicant: NATIONAL TSING HUA UNIVERSITY, Hsinchu (TW)

(72) Inventors: Hsing-Wen Sung, Hsinchu (TW); Wei-Chih Lin, New Taipei (TW); Shu-Jyuan Lin, Miaoli County (TW)

(73) Assignee: NATIONAL TSING HUA UNIVERSITY, Hsinchu (TW)

( * ) Notice: Subject to any disclaimer, the term of this patent is extended or adjusted under 35 U.S.C. 154(b) by 0 days.

(21) Appl. No.: 15/710,846

(22) Filed: Sep. 21, 2017

(65) Prior Publication Data
US 2018/0271789 A1    Sep. 27, 2018

(30) Foreign Application Priority Data
Mar. 22, 2017 (TW) .............................. 106109585 A

(51) Int. Cl.
| | |
|---|---|
| *A61K 9/00* | (2006.01) |
| *A61K 9/16* | (2006.01) |
| *A61K 33/04* | (2006.01) |
| *A61L 26/00* | (2006.01) |

(52) U.S. Cl.
CPC .......... *A61K 9/1617* (2013.01); *A61K 9/0014* (2013.01); *A61K 9/1682* (2013.01); *A61K 33/04* (2013.01); *A61L 26/00* (2013.01)

(58) Field of Classification Search
CPC .. A61K 9/0014; A61K 9/1617; A61K 9/1682; A61K 33/04; A61L 26/00
See application file for complete search history.

(56) References Cited

U.S. PATENT DOCUMENTS 6,046,243 A * 4/2000 Wellinghoff ........... A01N 59/00
514/772.3

FOREIGN PATENT DOCUMENTS

CN   105936756 A  *  9/2016

OTHER PUBLICATIONS

Industrial Waxes, Sasol Performance Chemicals—Technical Bulletin (Year: 2018).*
Ferris et al., "Composition of Paraffin Wax", Industrial Engineering Chem 21: 1090-1092 (1929) (Year: 1929).*
Wei-Chih Lin et al., "In situ depot comprising phase-change materials that can sustainably release a gasotransmitter H2S to treat diabetic wounds", Biomaterials, vol. 145, 8 pages, available online on Aug. 17, 2017, http://dx.doi.org/10.1016/j.biomaterials.2017.08.023.

* cited by examiner

*Primary Examiner* — John Pak
*Assistant Examiner* — Nathan W Schlientz
(74) *Attorney, Agent, or Firm* — CKC & Partners Co., LLC

(57) ABSTRACT

The present disclosure provides a sustained-release composition including a sodium hydrosulfide and a carrier. The carrier is provided for carrying the sodium hydrosulfide with an effective amount and includes a first component and a second component. The first component includes a paraffin wax, and the second component includes a fatty alcohol, a fatty acid or a phospholipid. The present disclosure also provides a method for fabricating the sustained-release composition. The method includes providing a first solution, providing the carrier, providing a second solution, performing an oil-in-water emulsification, and cooling the emulsion. In addition, the present disclosure provides a method for treating the chronic wounds. The method includes administering an effective amount of the aforementioned sustained-release composition to a subject suffered from the chronic wounds.

15 Claims, 15 Drawing Sheets

SUSTAINED-RELEASE COMPOSITION, METHOD FOR FABRICATING, AND USE THEREOF

RELATED APPLICATIONS

This application claims priority to Taiwan Application Serial Number 106109585, filed Mar. 22, 2017, which is herein incorporated by reference.

BACKGROUND

Technical Field

The present disclosure relates to a sustained-release composition. More particularly, the present disclosure relates to a sustained-release composition which is capable of producing hydrogen sulfide continuously, method for fabricating thereof and use the same.

Description of Related Art

There are about 422 million people with diabetes in the world and about 15% of these people are suffered from the chronic wounds, wherein the chronic wounds of the diabetic patients are called "diabetic ulcer". The persistent hyperglycemia inhibits cell migration, cell proliferation and collagen accumulation, thereby reducing the speed of angiogenesis. Therefore, debridement and glycemic control become the conventional primary treatment of the wounds on the diabetic patients. However, this treatment can not play too much effect because the wounds on the diabetic patients are not easy to heal over. Accordingly, the difficulty of tissue reorganization and the risk of infection are enhanced in the diabetic patients.

Hydrogen sulfide ($H_2S$) has been recognized as the third endogenous gaseous signaling molecule following nitric oxide (NO) and carbon oxide (CO), which can be endogenously produced in a variety of tissues and cells of mammals so as to be widely existed in various tissues. Recently, many researches processed by animal experiments have confirmed that hydrogen sulfide with a physiological concentration almost involves in all life activity processes, as well as the signaling molecules related to endothelial cell proliferation and migration, such as ERK1/2 and p38 can be phosphorylated by supplying the exogenous hydrogen sulfide, so as to activate the aforementioned signaling molecules and improve angiogenesis.

Sodium hydrosulfide (NaHS), an ionic compound with a simple structure and a low-cost price, can be converted into hydrogen sulfide in 100 percent after being reacted with water. Comparing with other common hydrogen sulfide precursors, such as (4-methoxyphenyl) morpholino-dithiophosphonic acid and morpholin-4-methoxyphenyl (morpholino) phosphinodithioate (GYY4137), sodium hydrosulfide does not produce any byproducts after reacting with water. However, sodium hydrosulfide will be converted into hydrogen sulfide rapidly and in a large quantity after exposing to water, so that the transient concentration of hydrogen sulfide in the human body is too high to provide a long-term treatment to the human body.

SUMMARY

According to one aspect of the present disclosure, a sustained-release composition includes a sodium hydrosulfide and a carrier for carrying the sodium hydrosulfide with an efficient amount. The carrier includes a first component and a second component, wherein the first component includes a paraffin wax, and the second component includes a fatty alcohol, a fatty acid or a phospholipid.

According to another aspect of the present disclosure, a method for fabricating the aforementioned sustained-release composition includes providing a first solution, providing the carrier, and processing a mixing step. In the step of providing a first solution, the first solution includes the sodium hydrosulfide. In the step of providing the carrier, the carrier is provided by mixing the first component and the second component, wherein the carrier is used as an oil phase. In the step of processing the mixing step, the mixing step is processed by mixing the first solution with the carrier, thus a mixture is obtained, and the mixture includes the aforementioned sustained-release composition.

According to another aspect of the present disclosure, a method for treating the chronic wounds includes administering an effective amount of the aforementioned sustained-release composition to a subject suffered from the chronic wounds.

BRIEF DESCRIPTION OF THE DRAWINGS

The present disclosure can be more fully understood by reading the following detailed description of the embodiment, with reference made to the accompanying, drawings as follows.

DETAILED DESCRIPTION

Figure 1:
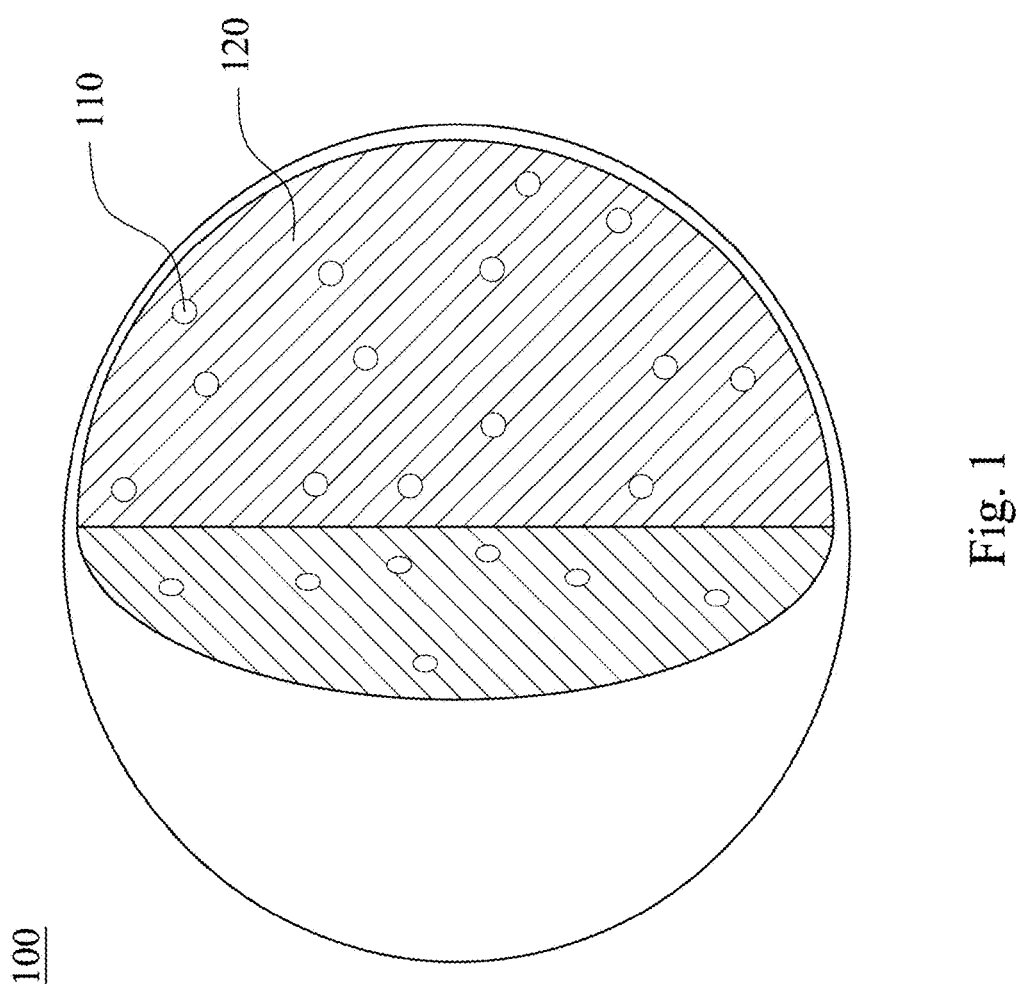
FIG. 1 is a structural schematic view of the sustained-release composition according to the present disclosure.

Please refer to FIG. 1, which is a structural schematic view of the sustained-release composition 100 according to the present disclosure. As shown in FIG. 1, the sustained-release composition 100 can be a microsphere and includes a sodium hydrosulfide 110 and a carrier 120. The carrier 120 is provided for carrying the sodium hydrosulfide 110. The carrier 120 includes a first component and a second component, wherein the first component includes a paraffin wax, and the second component includes a fatty alcohol, a fatty acid or a phospholipid.

In detail, the sustained-release composition according to the present disclosure is intended to be used as the pharmaceutical medicine for treating the chronic wounds, especially for treating the surface wounds. Because the temperature of the surface wounds is about 33° C., the melting point of the carrier 120 must be greater than or equal to 33° C. and can be dissolved in the aqueous solution in the preparing process. In other words, the melting point of the carrier 120 must be greater than or equal to 33° C. and less than the boiling point of water. However, the bubbles of water vapor generated approaching to the boiling point of water also affect the emulsifying efficiency of the carrier 120, so that the melting point of the carrier 120 is preferably less than or equal to 80° C. Thus, when the first component of the carrier 120 is the paraffin wax, the carrier 120 is represented by Formula (I):

(I), wherein m is 20 to 34. When the second component of the carrier 120 is the fatty alcohol, the carrier 120 is represented by Formula (II):

(II), wherein n is 13 to 25. Moreover, when the second component of the carrier 120 is the fatty acid, the carbon-number of the carrier is 10 to 20.

Furthermore, the aforementioned conditions can be also achieved by adjusting a weight ratio of the first component and the second component. In detail, the first component and the second component of the carrier 120 are contained in a weight ratio of 1:0.1 to 1:10.

In addition, the sustained-release composition of the present disclosure is a microsphere and can be fabricated by different emulsifying methods, such as homogeneous emulsification method, ultrasonic method or microfluidic channel method. The particle size of the aforementioned microsphere can be ranged from 5 μm to 300 μm.

Figure 2:
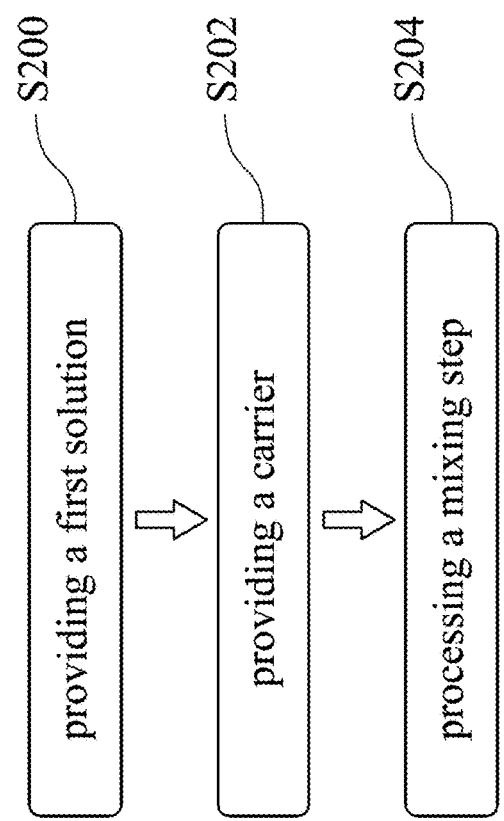
FIG. 2 is a flow chart of the method for fabricating the sustained-release composition according to the present disclosure.

Please refer to FIG. 2, which is a flow chart of the method for fabricating the sustained-release composition according to the present disclosure. The method for fabricating the sustained-release composition includes Step S200, Step S202, and Step S204.

Step S200 is providing a first solution, wherein the first solution includes the sodium hydrosulfide. In detail, the first solution is fabricated by dispersing the sodium hydrosulfide in a dehydrating agent. The dehydrating agent is used to remove the hydrated crystal of the sodium hydrosulfide, and then the sodium hydrosulfide can be decomposed into smaller particles so as to facilitate the wrapping of the sodium hydrosulfide within the carrier. In more detail, the dehydrating agent can be but not limited to ethanol or isopropanol.

Step S202 is providing the carrier. The carrier is provided by mixing the first component and the second component, wherein the carrier is used as an oil phase in the following emulsification method. In detail, the first component can be the paraffin wax, and the second component can be the fatty alcohol, the fatty acid or the phospholipid. The emulsification method can be but not limited to homogeneous emulsification method, ultrasonic method or micro flow channel method.

Step S204 is processing a mixing step by mixing the first solution with the carrier, thus a mixture is obtained, wherein the mixture contains the sustained-release composition of the present disclosure. In addition, in order to facilitate the reaction between the sodium hydrosulfide and the carrier, Step S204 can further include a heating step for heating the carrier. In detail, the heating step is heating the carrier until the carrier is melted, so that the sodium hydrosulfide and the carrier can be mixed homogeneously during the fabrication process.

Figure 3:
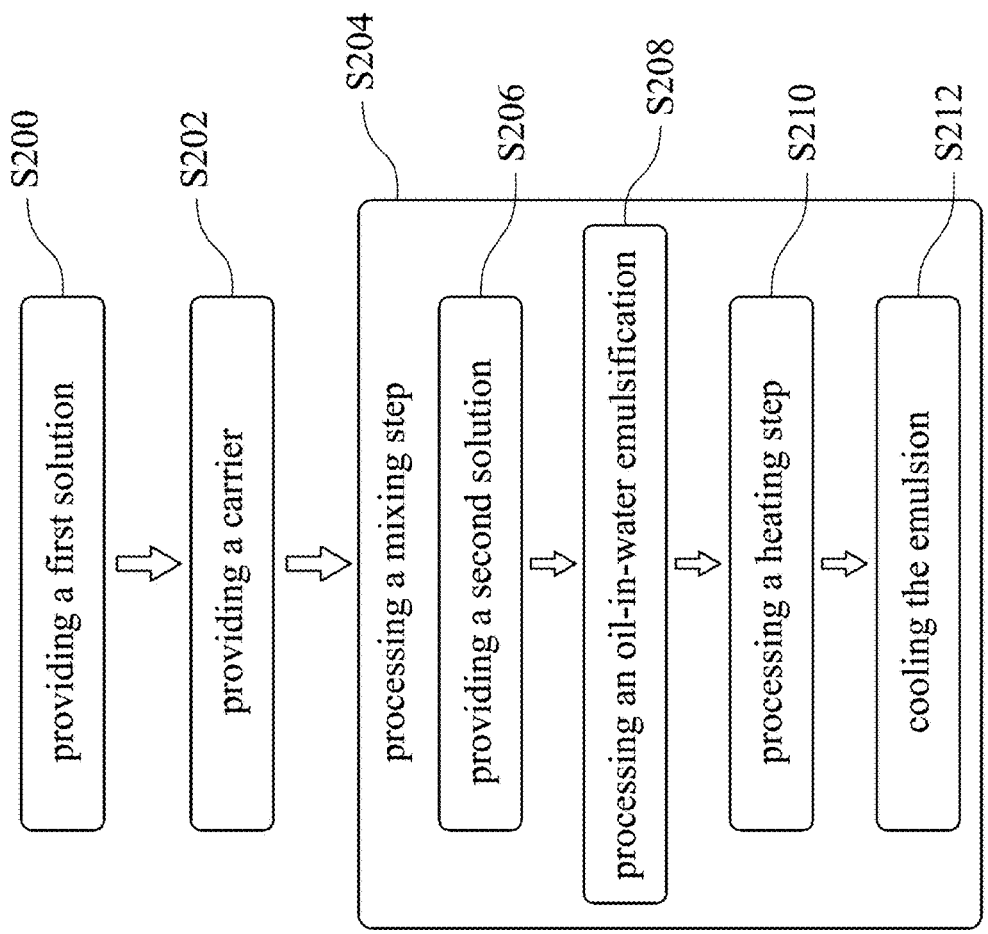
FIG. 3 is a flow chart of another method for fabricating the sustained-release composition according to the present disclosure.

Please refer to FIG. 3, which is a flow chart of another method for fabricating the sustained-release composition according to the present disclosure. In FIG. 3, the method for fabricating the sustained-release composition includes Step S200, Step S202 and Step S204, wherein Step S204 includes step 206, step 208, step 210 and step 212. The aforementioned Step S200 and Step S202 are the same with Step S200 and Step S202 described in FIG. 2 and not be described herein.

Step S206 is providing a second solution, and the second solution is used as a water phase in the following emulsification method. In detail, the second solution includes a water, a surfactant and a thickening agent, wherein the surfactant can be used to stabilize the molten-state structure of the carrier so as to prevent the carriers from collisions and aggregations, and the thickening agent can be used to adjust the viscosity of the second solution so as to enhance the dispersibility of the particles in the oil-in-water emulsification method. In detail, the surfactant can be but not limited to polyvinyl alcohol (PVA), tween 20, tween 80 or sodium dodecyl sulfate (SDS), and the thickening agent can be but not limited to alginate, gelatin, starch or carboxymethyl cellulose.

Step S208 is processing an oil-in-water emulsification by mixing the first solution with the carrier so as to obtain the mixture, and then the mixture is added into the second solution, thus an emulsion is obtained.

Step S210 is processing a heating step for heating the carrier and the second solution so as to facilitate the reaction among the sodium hydrosulfide, the carrier and the second solution in the first solution. In detail, the heating step is heating the carrier as well as the second solution until the carrier is melted, so that the sodium hydrosulfide and the carrier can be mixed homogeneously during the fabrication process.

Step S212 is cooling the emulsion. In detail, Step S208 is cooling the emulsion so as to facilitate the solidification of the oil phase, thus the sustained-release composition of the present disclosure is obtained. Thereafter, the sustained-release composition can be collected by filtrating process, washing process or drying process. At this time, since the sodium hydrosulfide is homogeneously mixed within the carrier in step S206, the sodium hydrosulfide of the sustained-release composition must be homogeneously dispersed within the carrier. The detailed fabricating method and the related fabricating conditions will be described in the following embodiments and not be described here.

Accordingly, the sustained-release composition fabricated by the aforementioned steps can be utilized as the drug ingredient for treating the related diseases, such as the chronic wounds. In detail, the aforementioned drug can further include a pharmaceutically acceptable salt, but the present disclosure is not limited thereto.

The sustained-release composition and fabricating method thereof will be further described by the following embodiments. In the following, a 1st embodiment, a 2nd embodiment, a 1st comparative embodiments and a 2nd comparative embodiment will be further provided to illustrate the accompanied efficacies of the sustained-release composition. However, the present disclosure is not limited thereto.

Sustained-Release Composition and Method for Fabricating Thereof

1st Embodiment

In the 1st embodiment, the sodium hydrosulfide is mixed with the ethanol in a weight ratio of 1:19.2 with agitation so as to disperse the sodium hydrosulfide in the ethanol sufficiently and then form the first solution. Thereafter, 0.1 g of the polyvinyl alcohol is dissolved in 10 mL of the deionized water (DI) and then 0.25 g of the alginic acid is added so as to fabricate an aqueous solution containing 1% of the polyvinyl alcohol and 2.5% of the alginic acid (the aqueous solution is the second solution). The aqueous solution is used as the water phase.

Next, 0.168 g of the first component and 0.168 g of the second component are mixed to form the oil phase. The first component is the paraffin wax and the second component is the 1-tetradcanol in the 1st embodiment, wherein the carbon-number of the paraffin wax is 24 to 26, and the paraffin wax and the 1-tetradcanol are contained in a weight ratio of 1:1.

Thereafter, the oil phase and the water phase prepared in the aforementioned steps are heated to 60° C. by the water bath. After reaching to 60° C., 85 µL of the first solution are added into the oil phase and agitated rapidly, and then the mixture of the first solution and the oil phase is added to the water phase with agitation by the stir bar. After the ethanol of the first solution is extracted into the water phase as well as the oil phase and the water phase are mixed to form a primary emulsion, the primary emulsion is slowly dropped into a cooling water in order to facilitate the solidification of the oil phase and then make the primary emulsion suspend in the cooling water. After finishing the cooling step, the primary emulsion will transform into the sustained-release composition of the present disclosure. Finally, the cooling water containing the sustained-release composition is passed through a filter paper with 6 µm pores by the suction filtration so as to remove the cooling water. The sustained-release compositions collected by the aforementioned steps are placed on the dish for drying along with the filter paper. After drying, the sustained-release composition collected by the aforementioned steps can be stored so as to apply to the following applications and analysis.

Figure 4A:
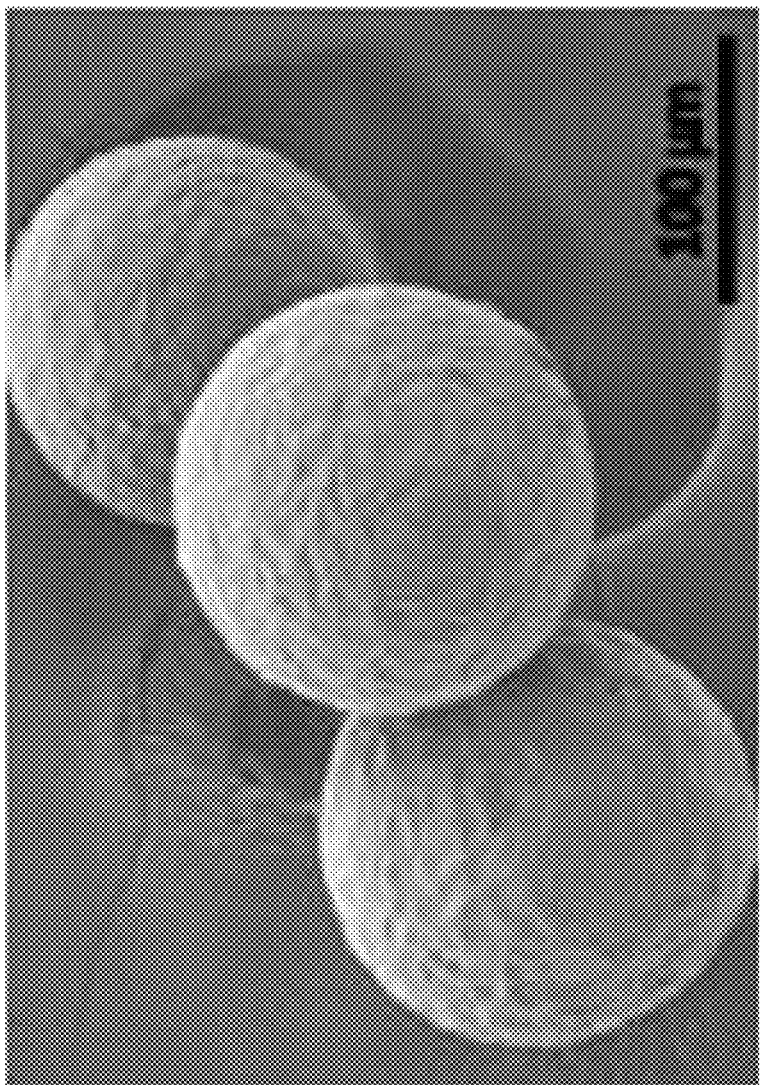
FIG. 4A is a scanning electron microscope image of the sustained-release compositions according to the 1st embodiment of the present disclosure.
Figure 4B:
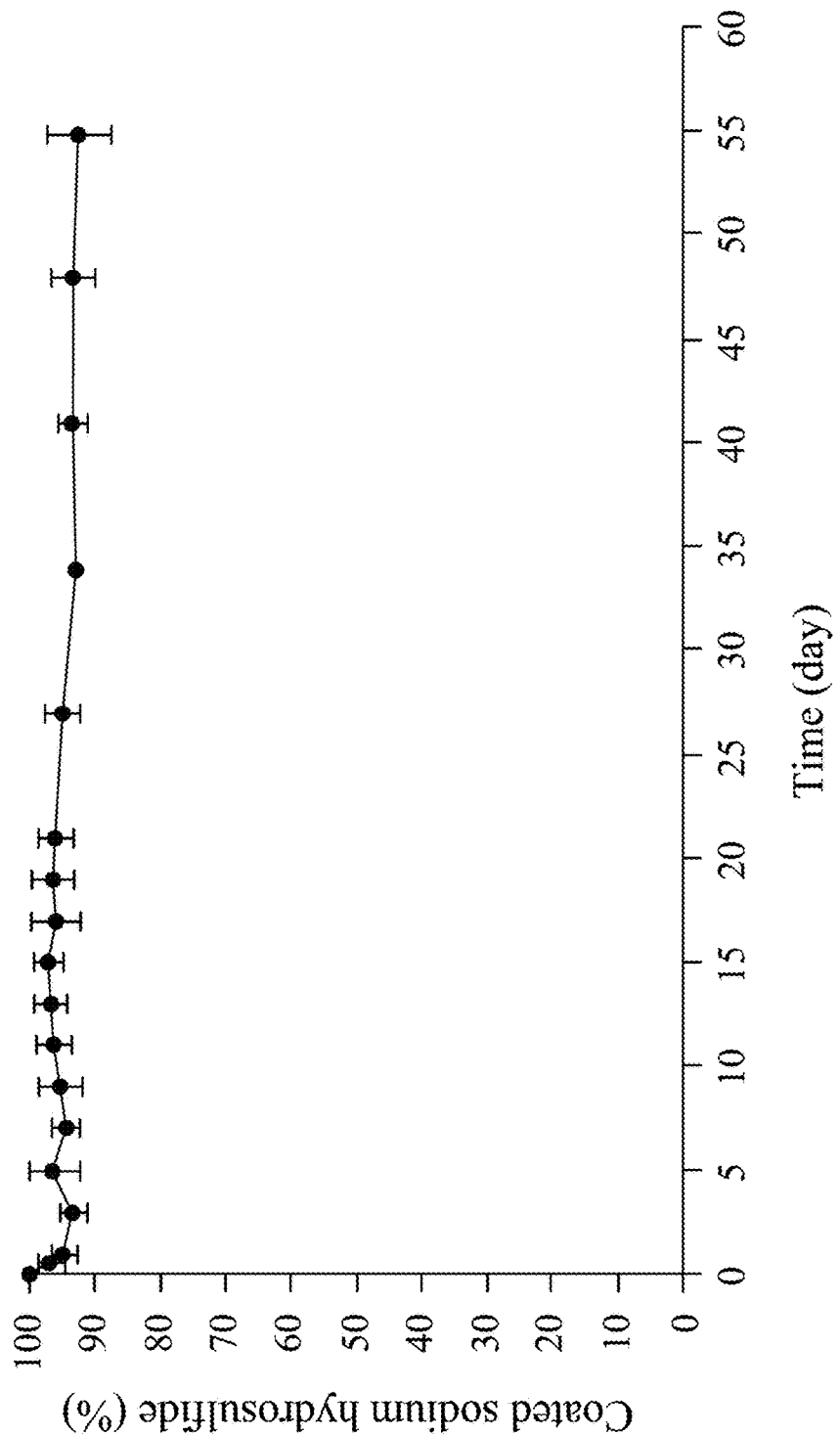
FIG. 4B is a block diagram showing the stability of the coated amount of the sodium hydrosulfide during the shelf life of the sustained-release composition according to the 1st embodiment of the present disclosure.

Please refer to FIG. 4A and FIG. 4B. FIG. 4A is a scanning electron microscope image of the sustained-release compositions according to the 1st embodiment of the present disclosure, and FIG. 4B is a block diagram showing the stability of the coated amount of the sodium hydrosulfide during the shelf life of the sustained-release composition according to the 1st embodiment of the present disclosure. As shown in FIG. 4A, the sustained-release composition is a microsphere with an average particle size of 148±37.2 µm. In the 1st embodiment, each microsphere (that is, each sustained-release composition) can contain 0.08 wt % of the sodium hydrosulfide.

As shown in FIG. 4B, when the sustained-release composition is stored in a vacuum environment at the room temperature, the encapsulated sodium hydrosulfide level of the sustained-release composition is kept more than 90%. That is, the sustained-release composition of the present disclosure can be stored at least for 8 weeks under the aforementioned condition. In addition, it must be noted that in order to avoid the gaseous hydrogen sulfide effusing from the sample bottle when the sample bottle is opened and then further effecting the experiment results, the sustained-release compositions of each tested sample of the 1st embodiment are stored in independent sample bottles respectively and prepared independently at each measured time. In other words, each sample bottle is opened and sampled only at the corresponding measured time.

2nd Embodiment

In the 2nd embodiment, the sodium hydrosulfide is mixed with the ethanol in a weight ratio of 1:19.2 with agitation so as to disperse the sodium hydrosulfide in the ethanol sufficiently and then form the first solution.

And then, 0.168 g of the first component and 0.168 g of the second component are mixed to form the oil phase. The first component is the paraffin wax and the second component is the 1-tetradcanol in the 2nd embodiment, wherein the carbon-number of the paraffin wax is 24 to 26, and the paraffin wax and the 1-tetradcanol are contained in a weight ratio of 1:1. Alternatively, the first component can be but not limited to paraffin wax, petrolatum and other ointments.

Next, the oil phase prepared in the aforementioned steps is heated to 60° C. by the water bath. After reaching to 60° C., the first solution is added into the oil phase with agitation by the stir bar, wherein the first solution and the carrier are contained in a weight ratio of 5:1. Thereafter, the first solution and the oil phase is mixed homogeneously so as to obtain a mixture. The mixture contains the sustained-release composition of the present disclosure.

Thereafter, the mixture is homogeneously dispersed on a substrate by film-forming methods, such as scraper coating method, spin coating method and spray coating method when the mixture is stilled in the melted state. After the mixture is cooled down and the ethanol contained in the mixture evaporates, the substrate contained the mixture can be used as a dressing and then applied to a subject directly. On the other hand, the mixture can be also placed in a centrifuge tube and treated with liquid nitrogen for 20 seconds so as to solidify the mixture. After solidifying, the mixture is taken out from the centrifuge tube and grinded by the cryogenic crusher. Thereafter, the mixture is transferred into a plurality of wax particles with a particle size ranges from 300 µm to 500 µm. After the wax particles are cooled down and the ethanol contained in the wax particles evaporates, the wax particles can be homogeneously dispersed on a substrate and then applied to a subject directly.

1st Comparative Embodiment

In the 1st comparative embodiment, the fabricating method of the sustained-release composition is similar with the aforementioned 1st embodiment, but the paraffin wax and the 1-tetradcanol of the carrier are contained in a weight ratio of 0:1 in the 1st comparative embodiment.

2nd Comparative Embodiment

In the 2nd comparative embodiment, the fabricating method of the sustained-release composition is similar with the aforementioned 1st embodiment, but the paraffin wax and the 1-tetradcanol of the carrier are contained in a weight ratio of 0:1 in the 2nd comparative embodiment.

Thereafter, it will be further confirmed by the 1st comparative embodiment and 2nd comparative embodiment that the sustained-release composition of the present disclosure can release the hydrogen sulfide slowly and continuously for achieving a long-term therapeutic effect.

Measure of the Sodium Hydrosulfide Release Curve

Figure 5:
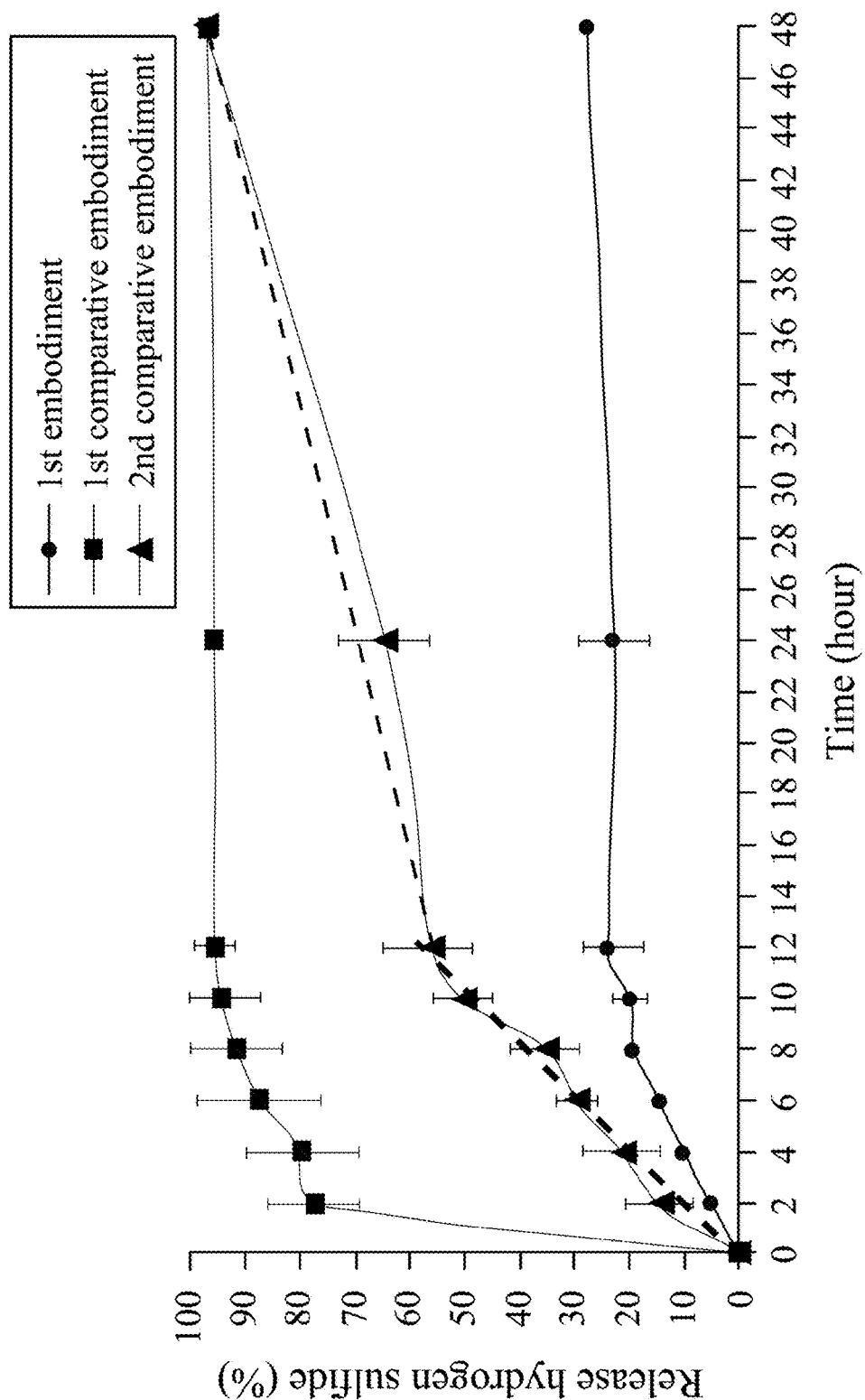
FIG. 5 is a release curve diagram of the hydrogen sulfide according to the 1st embodiment, the 1st comparative embodiment and the 2nd comparative embodiment of the present disclosure.

Please refer to FIG. 5, which is a release curve diagram of the hydrogen sulfide according to the 1st embodiment, the 1st comparative embodiment and the 2nd comparative embodiment of the present disclosure. In detail, the measuring method of the hydrogen sulfide release curve of the aforementioned embodiments is described blow. First, the sustained-release compositions of the aforementioned 1st embodiment, 1st comparative embodiment and 2nd comparative embodiment are placed in the buffer saline at 33° C. and pH 7.4 respectively, so as to simulate an open wound condition of the skin. Thereafter, at every hour during the experiment, 100 µL of the sample and 100 µL of the 1.0 wt % zinc acetate solution are mixed together, and then 40 µL of the premix solution of the dimethyl-4-phenylenediamine and the $FeCl_3$ is added and then reacted for 10 minutes. Finally, the absorption intensity at the wavelength of 670 nm of the methylene blue (product of the aforementioned reaction) is detected, and the concentration of the hydrogen sulfide is measured according to a calibration curve obtained from the results of the absorption intensity.

As shown in FIG. 5, the release curve of the hydrogen sulfide of the sustained-release composition can be divided into two stages: the hydrogen sulfide is accumulated quickly in the first stage and released slowly and continuously in the second stage. When the sustained-release composition is applied for treating chronic wound, the concentration of the hydrogen sulfide in the plasma can be raised quickly and accumulated. Then, the hydrogen sulfide can be released slowly and continuously for achieving a long-term therapeutic effect.

By contrast, in the 1st comparative embodiment, the hydrogen sulfide of the sustained-release composition contained the 1-tetradcanol in the carrier releases quickly, and the release amount of the hydrogen sulfide reaches to 95% to 100% within 12 hours. That is, the sustained-release composition of the 1st comparative embodiment cannot effectively reduce the release rate of the hydrogen sulfide and cannot provide the long-term therapeutic effect. In the 2nd comparative embodiment, although the release amount of the hydrogen sulfide of the sustained-release composition contained the paraffin wax in the carrier can be accumulated to 20% within 12 hours, the release amount of the hydrogen sulfide in the subsequent 12 hours to 48 hours is limited. In other words, the sustained-release composition of the 2nd comparative embodiment cannot effectively release the hydrogen sulfide.

Then, the effects of the sustained-release composition of the present disclosure for enhancing cell proliferation, cell migration, and for activating the signaling molecules (for example: ERK1/2 protein and p38 protein) so as to enhance the angiogenesis and the efficiency of wound healing are further confirmed by the experimental group 1 to 4. In detail, the experimental group 1 and the experimental group 2 provide the sodium hydrosulfide aqueous solutions (not carried by the carrier) with an initial concentration of 150 µM and 300 µM respectively, the experimental group 3 provides 20 mg/mL of the sustained-release composition of the present disclosure, and the experimental group 4 provides 20 mg/mL of the carrier without the sodium hydrosulfide. In addition, a control group is further included in this experiment, wherein the control group is without any treatment and not provided with any formula.

In Vitro Cell Proliferation Test

The in vitro cell proliferation test is used the formulas of the aforementioned experimental groups 1 to the experimental 4 to treat the in vitro cultured cell respectively, and then a number of the survival cell are measured for 48 hours so as to establish the standards of the estimation of the ability for enhancing cell proliferation of the sustained-release composition of the present disclosure.

In this experiment, the tested cell is human umbilical vein endothelial cell (HUVEC) and the culture medium is Medium 199 (Invitrogen, Carlsbad, Calif., USA), wherein Medium 199 contains 10% of the fetal bovine serum (FBS), 30 µg/mL of the endothelial cell growth supplement (Millipore, Billerica, Mass., USA), 25 U/mL of the heparin (Sigma-Aldrich, St. Louis, Mo., USA), 2 mM of the L-glutamine, 100 U/mL of the penicillin, and 100 mg/mL of the streptomycin (Invitrogen). In order to simulate the hyperglycemia condition of the diabetic patients, the cells are treated in advance for 3 days with a medium containing 25 mM D-glucose in this experiment. In addition, all cells are incubated in an incubator which is 37° C. and contains 5% carbon dioxide and 95% air.

Thereafter, the human umbilical vein endothelial cells are seeded in a 96-well plate in a density of $10^3$ cells per well and incubated for 24 hours in the incubator until the cells attach to the bottom of the well. After incubating for 24 hours, the original medium is removed from the well and replaced with a new medium which contains the formula according to the aforementioned experimental group 1 to 4 (also containing 25 mM D-glucose). And then, after 48 hours treatment, the WST-1 reagent is added to each well and then reacted for 4 hours. In detail, the WST-1 reagent is a red, water-soluble tetrazolium salt solution, and after the WST-1 reagent is metabolized by the living cells, the tetrazolium salt of the WAS-1 reagent can be transformed into formazan which is an orange-yellow and water-soluble compound. The formazan has a light absorption peak at a wavelength of 440 nm so that the cell viability can be measured by the absorbed intensity of the formazan. Thus, the absorption intensity at a wavelength of 440 nm can be detected by a spectrometer (Spectra Max M5, Molecular Devices, Sunnyvale, USA) after the reaction is completed.

Figure 6:
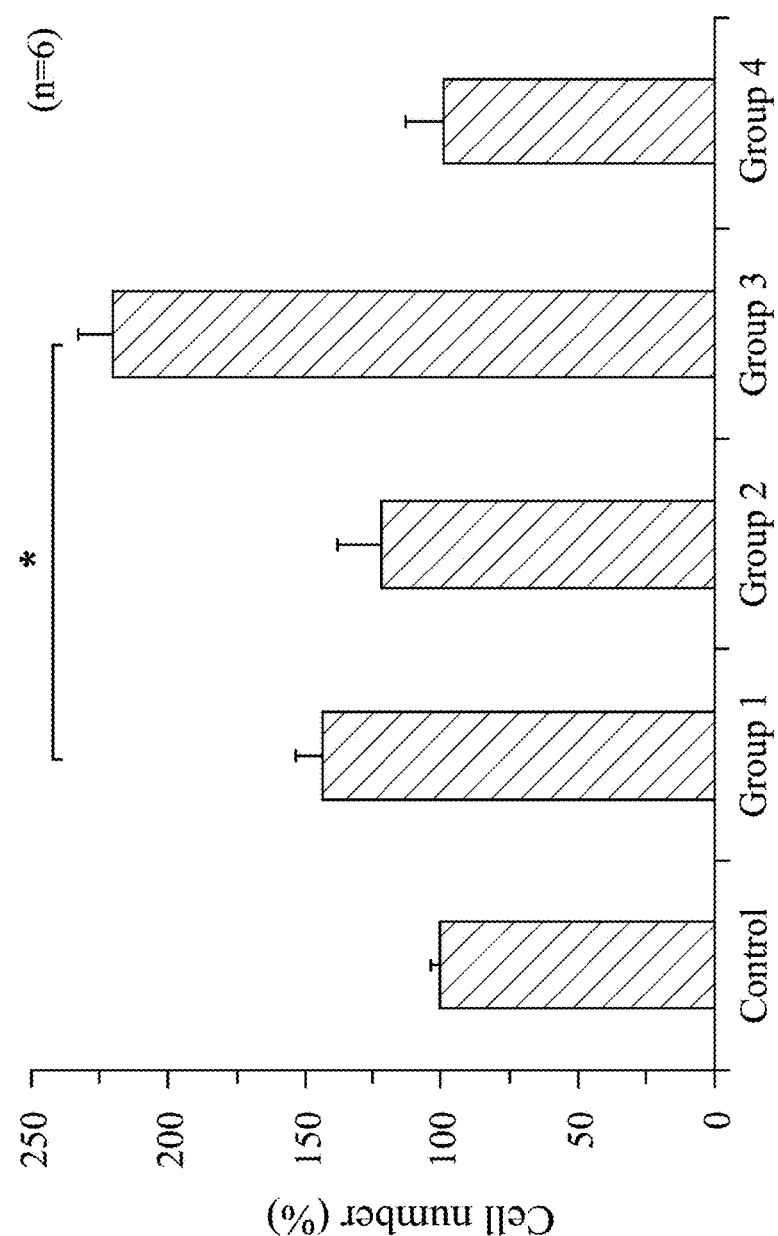
FIG. 6 is a result histogram showing the cell proliferation percentage of the human umbilical vein endothelial cells treated with the sustained-release composition formulas according to the experimental group 1 to the experimental group 4 of the present disclosure.

Please refer to FIG. 6, which is a result histogram showing the cell proliferation percentage of the human umbilical vein endothelial cells treated with the sustained-release composition formulas according to the experimental group 1 to the experimental group 4 of the present disclosure. In FIG. 6, the vertical axle of the result histogram represents the percentage of the living cell number compared with the control group, and the percentage of the living cell number of the control group is 100%. As shown in FIG. 6, after incubating for 48 hours, the percentage of the living cell number of the experimental group 3 is 2 to 2.5 times greater than the control group. It is confirmed that the sustained-release composition of the present disclosure is capable to enhance the proliferation of the cells exactly. In addition, the cell proliferation enhancing ability of the sustained-release composition of the present disclosure is better than the experimental group 1 and the experimental group 2 treated with the sodium hydrosulfide directly.

Tubular Structure Formation Test of the Human Umbilical Vein Endothelial Cell

The human umbilical vein endothelial cells will migrate, arrange and form a tubular network structure without additional growth factors and the participation of other kinds of cells, thus the wound-healing efficiency is affected by the maintenance of the tubular structure of the cells as time goes on. Therefore, the ability to enhance cell migration and facilitate the angiogenesis of the sustained-release composition of the present disclosure is confirmed by the tubular structure formation test of the human umbilical vein endothelial cells. The specific experimental method is described below. First, 200 μL of the growth factor-reduced matrix Matrigel is added to each well of a 24-well plate respectively and then placed into the 37° C. incubator. After the growth factor-reduced matrix Matrigel is heated and become colloid, $2.5 \times 10^4$ of the human umbilical vein endothelial cells are seeded in each well of the aforementioned 24-well plate and then 200 μL of the medium (containing 25 mM D-glucose) is added to the wells respectively. The aforementioned mediums contain the formulas of the experimental group 1, the experimental group 3, and the control group respectively. Next, the tubular structure of each experimental group is observed via an inverted microscope at the time points of 6 hours, 12 hours, 24 hours and 48 hours, and the branching point number of each experimental group is calculated.

Figure 7A:
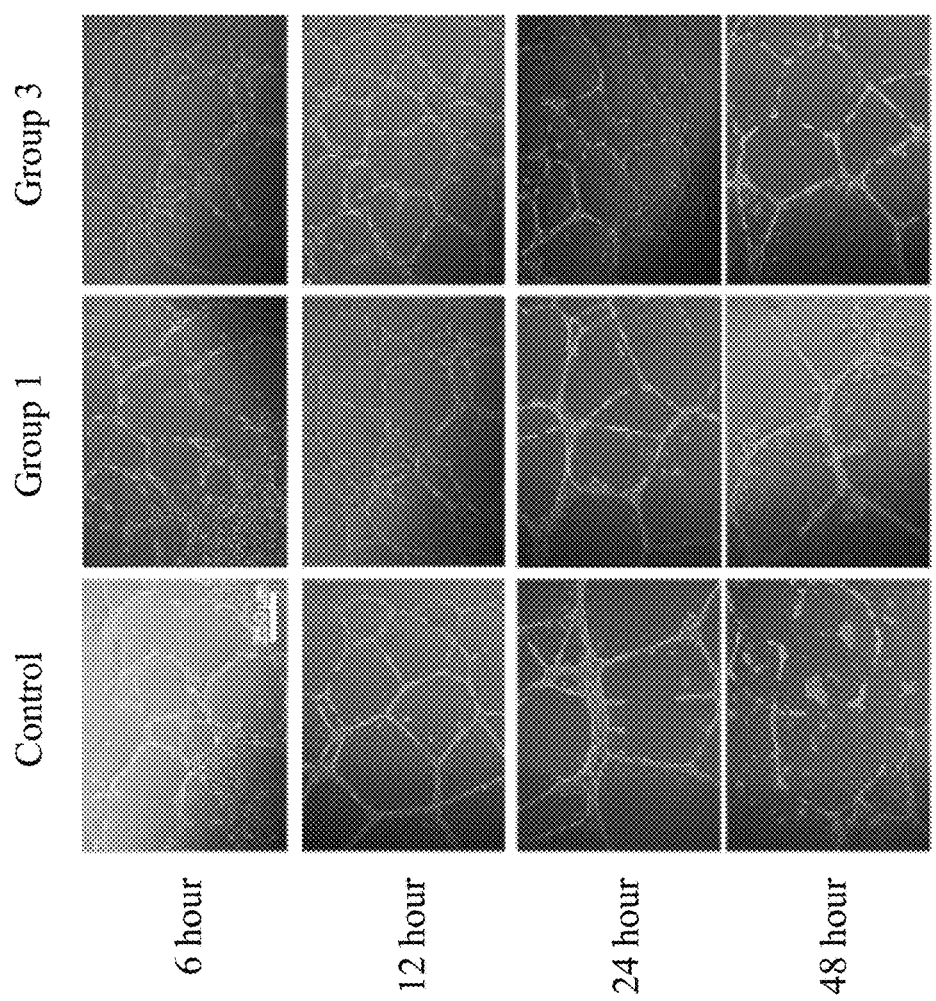
FIG. 7A is an optical microscope image showing the cell tubular structure formation of the human umbilical vein endothelial cells treated with the sustained-release composition formulas according to the experimental group 1 and the experimental group 3 of the present disclosure.
Figure 7B:
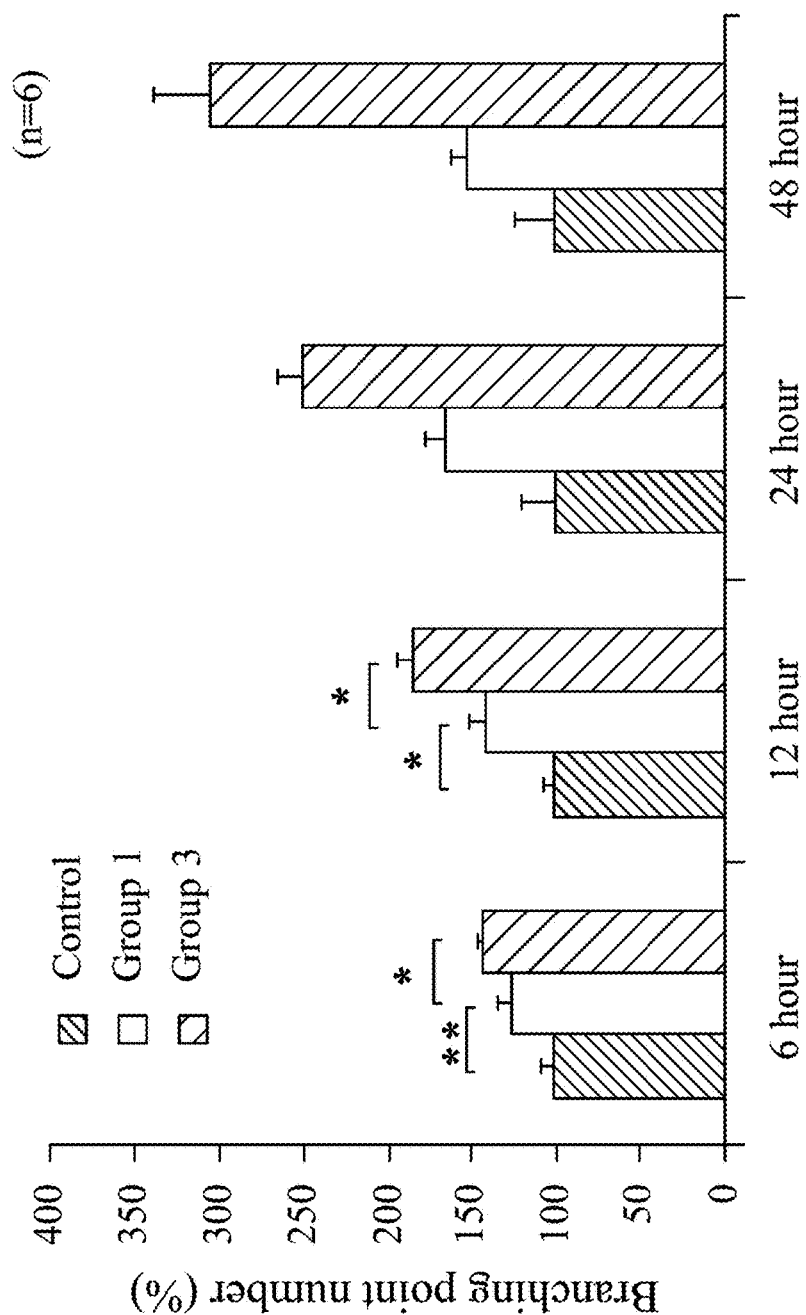
FIG. 7B is a result histogram showing the branching point number of the tubular structure of the human umbilical vein endothelial cells at each time point of FIG. 7A.

Please refer to FIG. 7A and FIG. 7B. FIG. 7A is an optical microscope image showing the cell tubular structure formation of the human umbilical vein endothelial cells treated with the sustained-release composition formulas according to the experimental group 1 and the experimental group 3 of the present disclosure, and FIG. 7B is a result histogram showing the branching point number of the tubular structure of the human umbilical vein endothelial cells at each time point of FIG. 7A. As shown in FIG. 7A, the tubular structure can be observed in the control group, the experimental group 1 and the experimental group 3 after incubating for 6 hours. After continuously incubating for a period of time, the tubular structure of the human umbilical vein endothelial cells will gradually disappear as time goes on. However, the tubular structure disappeared rates of the experimental group 1 and the experimental group 3 are reduced, wherein the tubular structure of the experimental group 3 (containing the sustained-release composition of the present disclosure) can be kept for the longest time period. Thus, the sustained-release composition of the present disclosure can help maintain the tubular structure of the human umbilical vein endothelial cells. In addition, as shown in FIG. 7B, the branching point number of the experimental group 3 is the highest at each time point. Therefore, the sustained-release composition of the present disclosure does have the ability to enhance cell migration and to facilitate the angiogenesis.

Cell Migration Test of the Skin Keratinocyte

The cell migration enhancing ability of the sustained-release composition of the present disclosure is further confirmed by the cell migration test of skin keratinocytes. The specific experimental method is described below. The cell migration test of the skin keratinocytes and the human umbilical vein endothelial cells are processed in a plate with a culture-insert (Ibidi, Martinsried, Germany). First, 70 μL of a cell suspension with a cell concentration of $2.86 \times 10^5$ cells/mL of the skin keratinocytes or the human umbilical vein endothelial cells is added to each chamber of the culture-insert, respectively. After incubating for 12 hours, the cells have already attached to the bottom of the plate, and then the culture-insert is removed so as to form a 500 μm intermediate gap 200 (the skin keratinocytes) or an intermediate gap 200' (the human umbilical vein endothelial cells) between two cell groups seeded in each chamber respectively. After removing the culture-insert and washing three times with the PBS, the 1% FBS mediums containing the formula according to the experimental group 1, the experimental group 2 and the experimental group 3 respectively (all of the medium contain 25 mM D-glucose) are added to different wells of the plate. This experiment further includes a control group which is without any treatment. Finally, the decrease degree of the intermediate gap of each experiment group is observed via the inverted microscope after 24 hours, and the area of the intermediate gap is measured by the image analysis software.

Figure 8A:
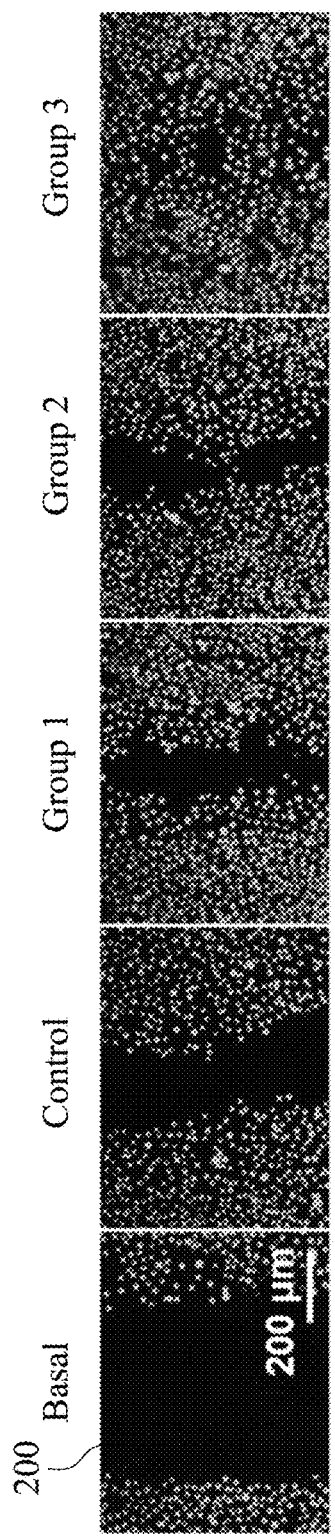
FIG. 8A is an optical microscope image showing the migration of the skin keratinocytes treated with the sustained-release composition formulas according to the basal group, the control group and the experimental group 1 to the experimental group 3 of the present disclosure.
Figure 8B:
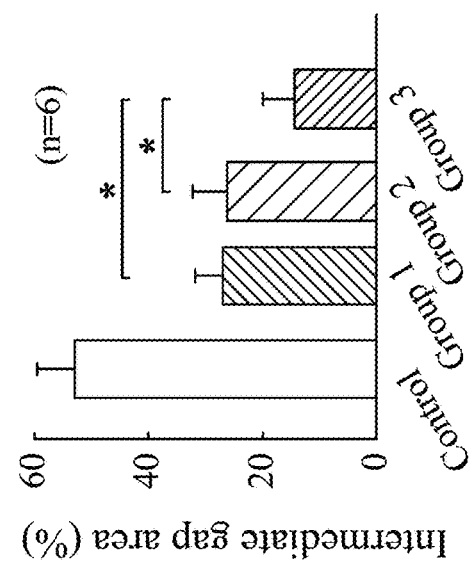
FIG. 8B is a result histogram showing the quantitative results of FIG. 8A.
Figure 8C:
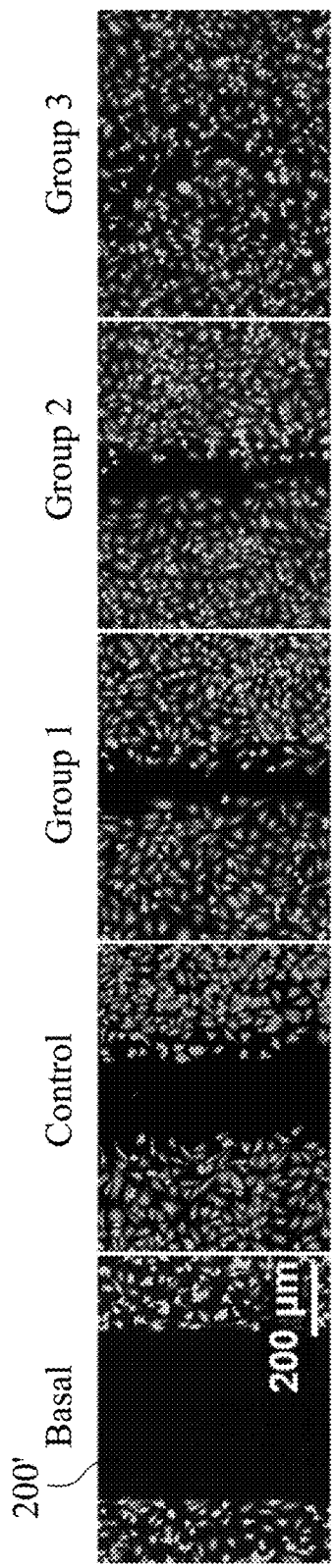
FIG. 8C is an optical microscope image showing the migration of the human umbilical vein endothelial cell treated with the sustained-release composition formulas according to the basal group, the control group and the experimental group 1 to the experimental group 3 of the present disclosure.
Figure 8D:
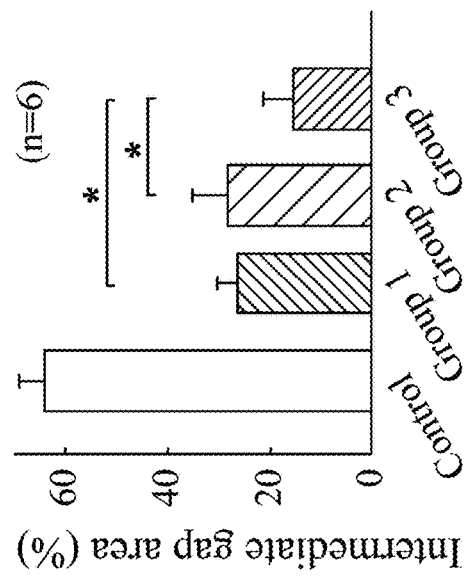
FIG. 8D is a result histogram showing the quantitative results of FIG. 8C.

Please refer to FIG. 8A to FIG. 8D. FIG. 8A is an optical microscope image showing the migration of the skin keratinocytes treated with the sustained-release composition formulas according to the basal group, the control group and the experimental group 1 to the experimental group 3 of the present disclosure, FIG. 8B is a result histogram showing the quantitative results of FIG. 8A, FIG. 8C is an optical microscope image showing the migration of the human umbilical vein endothelial cell treated with the sustained-release composition formulas according to the basal group, the control group and the experimental group 1 to the experimental group 3 of the present disclosure, and FIG. 8D is a result histogram showing the quantitative results of FIG. 8C. More particularly, as shown in FIG. 8A and FIG. 8C, the optical microscope images arranged in an order from left to right represent the basal group (the initial state of the intermediate gap), the control group (without any treatment), the experimental group 1 (containing the formula of the aforementioned experimental group 1), the experimental group 2 (containing the formula of the aforementioned experimental group 2) and the experimental group 3 (containing the formula of the aforementioned experimental group 3) after incubating for 24 hours respectively.

As shown in FIG. 8A, in contrast to the control group, the skin keratinocytes migrate to the intermediate gap 200 in all the experimental groups with the presence of the sodium hydrosulfide. Particularly, cells in the experimental group 3 (containing 20 mg/mL of the sustained-release composition of the present disclosure) migrate to the intermediate gap 200 significantly so that the intermediate gap 200 becomes unobvious. In FIG. 8B, the quantitation result histogram shows that the area of the intermediate gap 200 of the experimental group 3 has decreased to less than 20% compared with the initial area of the basal group. The quantitative results shown in FIG. 8B match to the results shown in FIG. 8A.

In addition, as shown in FIG. 8C, the human umbilical vein endothelial cells also migrate to the intermediate gap 200' with the presence of the sodium hydrosulfide. Particularly, cells in the experimental group 3 (containing 20 mg/mL of the sustained-release composition of the present disclosure) significantly migrate to the intermediate gap 200' so that the intermediate gap 200' becomes unobvious. In FIG. 8D, the quantitation result histogram shows that the area of the intermediate gap 200 of the experimental group 3 has decreased to less than 20% compared with the initial value of the basal group. The quantitative results shown in FIG. 8D match to the results shown in FIG. 8C. Therefore, the sustained-release composition of the present disclosure can effectively enhance the cell migration no matter to the skin keratinocytes or to the human umbilical vein endothelial cells. The sustained-release composition of the present disclosure used as the drug for treating the chronic wound can facilitate the healing of the wounds.

Signaling Molecule Activation Test

In the aforementioned description, the exogenous hydrogen sulfide can activate the signaling molecules related to the proliferation and the migration of the endothelial cells, such as ERK1/2 protein and p38 protein, so that the angiogenesis of the cells is enhanced. Thus, the ability to activate the signaling molecule of the sustained-release composition of the present disclosure is further estimated in this experiment. First, the human umbilical vein endothelial cells are seeded in a 6-well plate in a density of $10^5$ cells per well. After incubating for 24 hours, the 1% FBS mediums containing the formula of the experimental group 1 or the experimental group 3 (all of them contain 25 mM D-glucose) respectively is added to each well of a 6-wells-plate. Finally, the cells are collected at specific time points and the phosphorylation level of p38 protein and ERK1/2 are quantified by the enzyme-linked immunosorbent assay (ELISA).

Figure 9A:
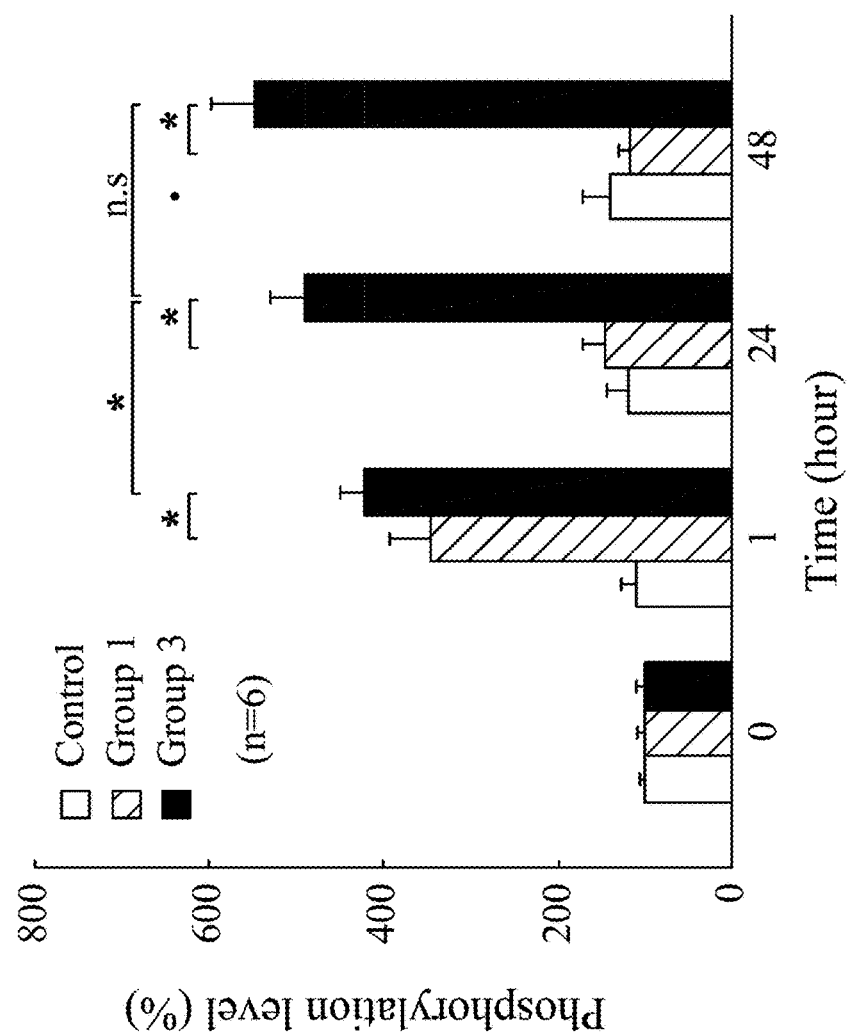
FIG. 9A is a histogram showing the phosphorylation level of p38 protein at different time points of the human umbilical vein endothelial cell treated with the sustained-release composition formulas according to the control group and the experimental group 1 to the experimental group 3 of the present disclosure.
Figure 9B:
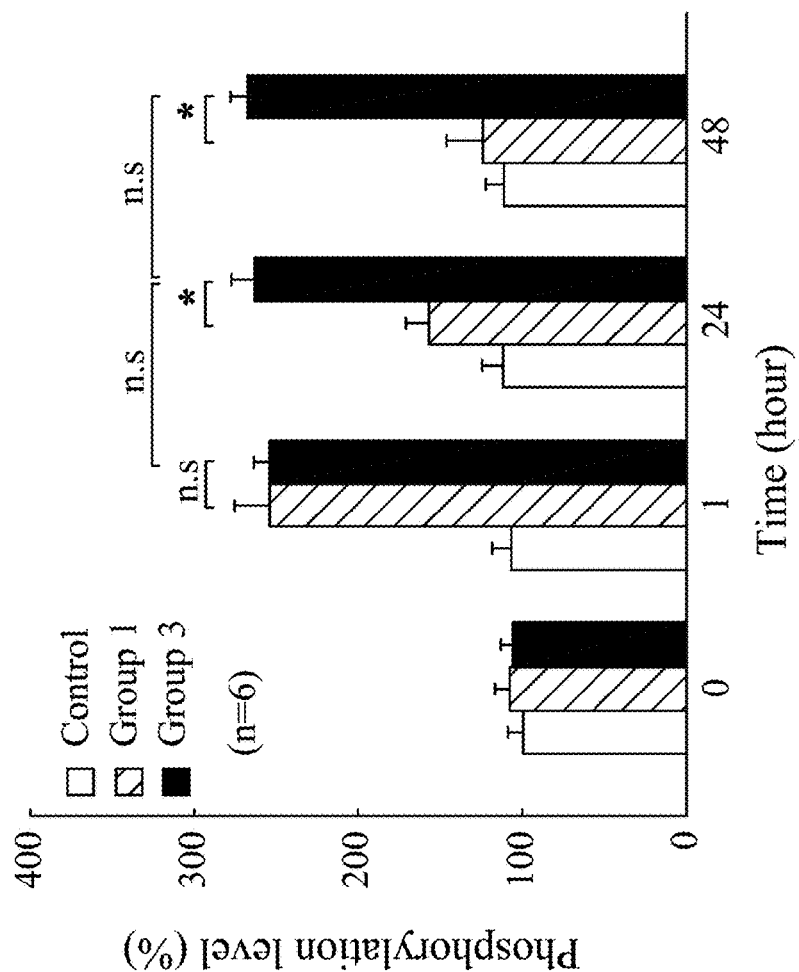
FIG. 9B is a histogram showing the phosphorylation level of ERK 1/2 protein at different time points of the human umbilical vein endothelial cell treated with the sustained-release composition formulas according to the control group and the experimental group 1 to the experimental group 3 of the present disclosure.

Please refer to FIG. 9A and FIG. 9B. FIG. 9A is a histogram showing the phosphorylation level of p38 protein at different time points of the human umbilical vein endothelial cell treated with the sustained-release composition formulas according to the control group and the experimental group 1 to the experimental group 3 of the present disclosure, and FIG. 9B is a histogram showing the phosphorylation level of ERK 1/2 protein at different time points of the human umbilical vein endothelial cell treated with the sustained-release composition formulas according to the control group and the experimental group 1 to the experimental group 3 of the present disclosure. As the results of the experimental group 1 shown in FIG. 9A, the sodium hydrosulfide carried by the carrier will decompose quickly and then release large amounts of the hydrogen sulfide so that the phosphorylation level of the p38 protein is significantly increased in the first hour during the cultural period. However, after incubating for 24 hours and 48 hours, the phosphorylation level of the p38 protein is decreased. Thereafter, as the results of the experimental group 3 shown in FIG. 9A, the sustained-release composition of the present disclosure can slowly and continuously release the hydrogen sulfide, so that the phosphorylation level of the p38 protein in the experimental group 3 can increase alone with the experimental time. The results of the phosphorylation level of the p38 protein of the experimental group 3 approximately match to the results of the hydrogen sulfide release curve of the sustained-release composition in the aforementioned 1st embodiment shown in FIG. 5.

Similarly, as the results of the experimental group 1 shown in FIG. 9B, the sodium hydrosulfide which is not carried by the carrier will decompose quickly and then release large amounts of the hydrogen sulfide so that the phosphorylation level of the ERK1/2 protein is significantly increased in the first hour during the cultural period. However, after incubating for 24 hours and 48 hours, the phosphorylation level of the ERK1/2 protein is decreased. Thereafter, as the results of the experimental group 3 shown in FIG. 9B, the sustained-release composition of the present disclosure can slowly and continuously release the hydrogen sulfide, so that the phosphorylation level of the ERK1/2 protein of the experimental group 3 can increase alone with the experimental time. The results of the phosphorylation level of the ERK1/2 protein in the experimental group 3 approximately match to the results of the hydrogen sulfide release curve of the sustained-release composition in the aforementioned 1st embodiment shown in FIG. 5.

In Vivo Wound Healing Test

According to the aforementioned results, the sustained-release composition of the present disclosure does have the ability to enhance the cell migration, the cell proliferation and the angiogenesis, and the ability to facilitate the wound healing of the sustained-release composition of the present disclosure is further confirmed by the following in vivo wound healing test. The animal model established method and the animal experiment procedures of the in vivo wound healing test in this experiment are complied with the "Laboratory Animal Care and Use Guide" published by the Council of Agriculture, Taiwan. The diabetic animal model used in this experiment is an 8-week-old BKS.Cg-Lepr$^{db}$/Lepr$^{db}$/JNarl mouse (also known as db/db mouse).

In the in vivo wound healing test, four symmetrically distributed rounded full-thickness wounds are created on the back skin of each mouse by the tissue sampler after the mice are anesthetized, wherein the diameter of each wound is 0.5 centimeter and the volume of each wound is 50 µL. The four wounds are applied with different treatments respectively and the dressing is replaced every 48 hours. There are three treatments in this experiment, one is the control group which is applied 50 µL of the normal saline to the wound and then covered with a breathable dressing (Tegaderm™, 3M), another is applied 50 µL of the formula according to the aforementioned experimental group 1 (that is, 150 µM of the sodium hydrosulfide aqueous solution) and then covered with a breathable dressing, and the other is uniformly distributed 1 mg of the formula according to the aforementioned experimental group 3 (that is, the sustained-release composition of the present disclosure) on a breathable dressing and then the aforementioned breathable dressing is covered upon the wound. In addition, after establishing the wounds, each mouse is raised in different cages so as to reduce the possibility of interferences to the wounds. And, the image of each wound is taken by the digital camera before replacing the dressing every time, and a key ring with a diameter of 15 mm is placed around the wound in order to serve as a scale while taking the images. The area changes of each wound at different time points are further analyzed by the image analysis software.

Figure 10A:
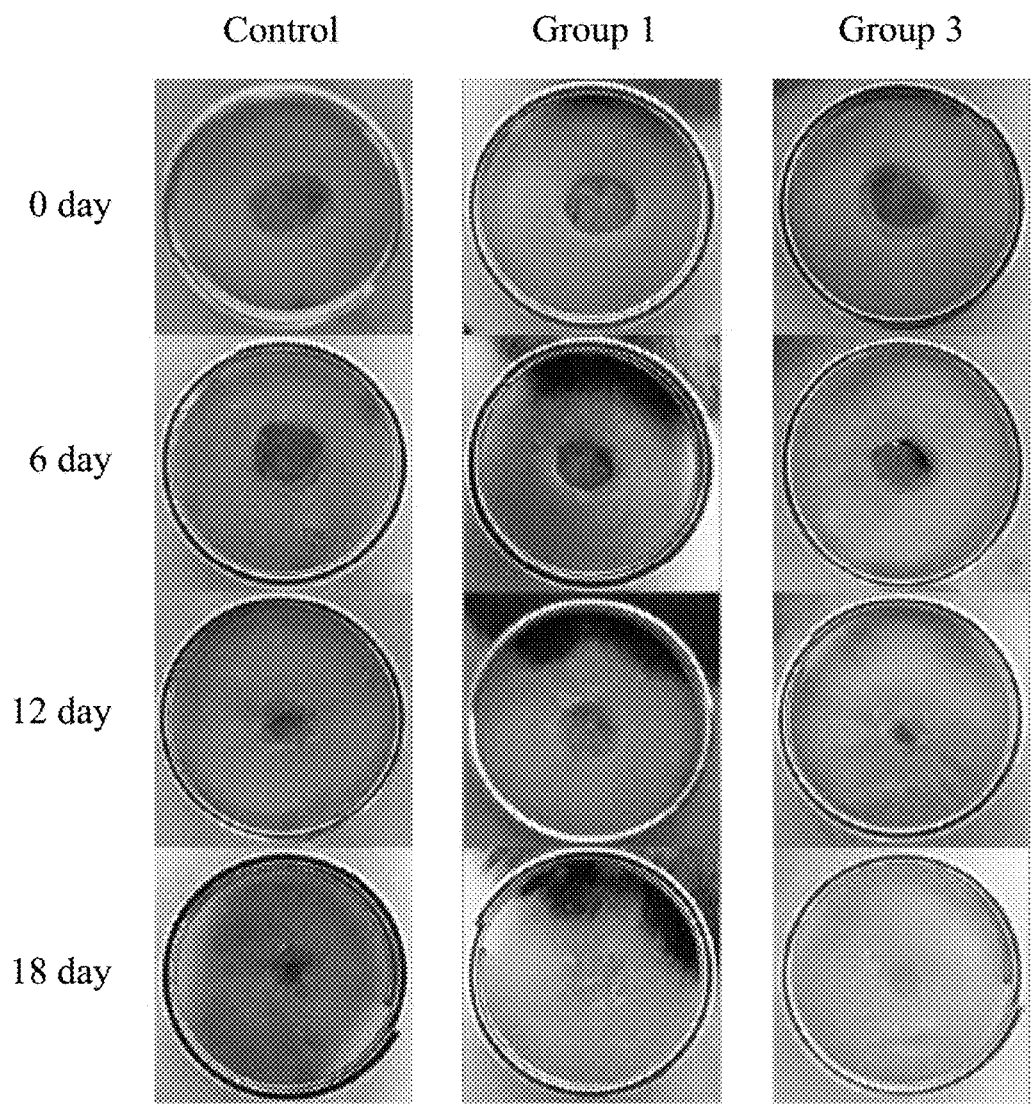
FIG. 10A is an image of the wound healing condition at different time points in the wound healing test after being treated with the sustained-release composition formulas according to the control group and the experimental group 1 to the experimental group 3 of the present disclosure.
Figure 10B:
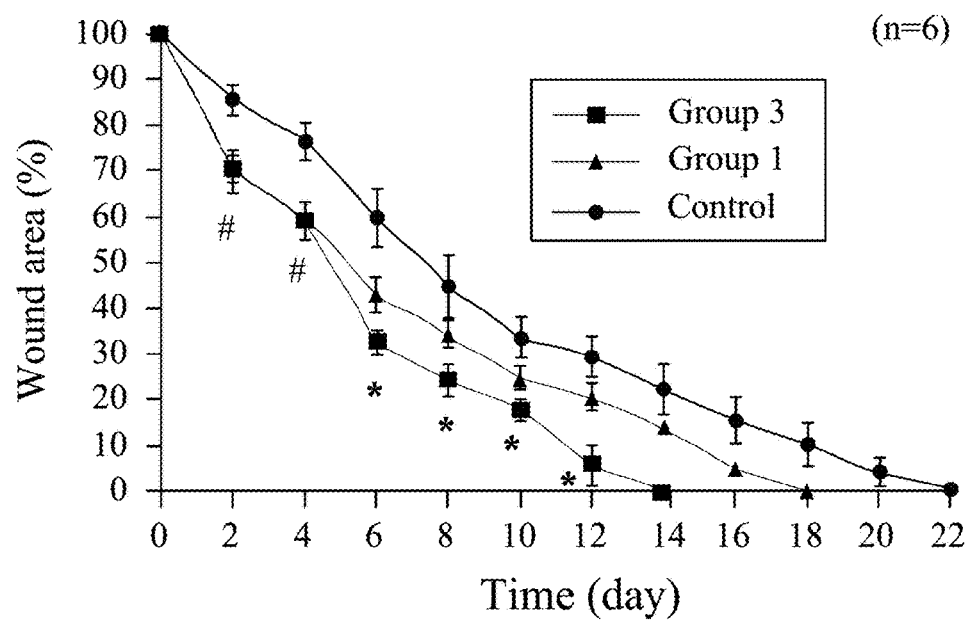
FIG. 10B is a result diagram showing the relationship between the wound area and the treated time in the wound healing test after being treated with the sustained-release composition formulas according to the control group and the experimental group 1 to the experimental group 3 of the present disclosure.

Please refer to FIG. 10A and FIG. 10B. FIG. 10A is an image of the wound healing condition at different time points in the wound healing test after being treated with the sustained-release composition formulas according to the control group and the experimental group 1 and the experimental group 3 of the present disclosure, and FIG. 10B is a result diagram showing the relationship between the wound area and the treated time in the wound healing test after being treated with the sustained-release composition formulas according to the control group and the experimental group 1 and the experimental group 3 of the present disclosure. As shown in FIG. 10A, the wound area of different wounds treated with the formulas according to the control group, the experimental group 1 and the experimental group 3 respectively is gradually decreased along with the time. However, as the wound images shown in FIG. 10A, the wound of the control group is still obvious after treating for 18 days, but the wound of the experimental group 1 and the experimental group 3 is unobvious. According to the aforementioned results, the hydrogen sulfide plays a certain role in the healing of the wound.

Please refer to FIG. 10A and FIG. 10B simultaneously. As shown in FIG. 10B, the wound area at the 14th day of the experimental group 3 is 0 compared with the initial time point (day 0). That is, the wound is completely healed. On the other hand, the wound treated with the formula according to the experimental group 1 is just completely healed at the 18th day. Therefore, the sustained-release composition of the present disclosure can slowly and continuously release the hydrogen sulfide, and the efficacy to heal the wounds is more significant than the sodium hydrosulfide which is not carried by the carrier.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A sustained-release composition, comprising:
    a therapeutically effective amount of sodium hydrosulfide; and
    a carrier for carrying the sodium hydrosulfide, the carrier comprising a first component and a second component, wherein the first component comprises a paraffin wax and the second component comprises a fatty alcohol, wherein the fatty alcohol of the carrier is represented by Formula (II):

$$CH_3(CH_2)_n OH \qquad (II),$$

wherein n is 13 to 25.

2. The sustained-release composition of claim 1, wherein a melting point of the carrier is greater than or equal to 33° C.

3. The sustained-release composition of claim 2, wherein the paraffin wax of the carrier is represented by Formula (I):

$$C_m H_{2m+2} \qquad (I),$$

wherein m is 20 to 34.

4. The sustained-release composition of claim 1, wherein the first component and the second component of the carrier are contained in a weight ratio of 1:0.1 to 1:10.

5. The sustained-release composition of claim 1, wherein the sustained-release composition is a microsphere with a particle size ranged from 5 μm to 300 μm.

6. A method for fabricating the sustained-release composition of claim 1, comprising the following steps:
    providing a first solution, wherein the first solution comprises a therapeutically effective amount of the sodium hydrosulfide;
    providing the carrier by mixing the first component and the second component, wherein the carrier is used as an oil phase;
    mixing the first solution with the carrier, heating to melt the carrier, then cooling to obtain a mixture, wherein the mixture comprises the sustained-release composition.

7. The method of claim 6, wherein the first solution is fabricated by dispersing the sodium hydrosulfide in a dehydrating agent.

8. The method of claim 7, wherein the first component and the second component of the carrier are contained in a weight ratio of 1:0.1 to 1:10.

9. The method of claim 8, wherein a melting point of the carrier is greater than or equal to 33° C.

10. The method of claim 9, wherein the paraffin wax of the carrier is represented by Formula (I):

$$C_m H_{2m+2} \qquad (I),$$

wherein m is 20 to 34.

11. The method of claim 9, wherein the step of mixing the first solution with the carrier comprises the following steps:
    providing a second solution, wherein the second solution is a water phase;
    mixing the first solution with the carrier so as to obtain the mixture, and then the mixture is added into the second solution, thus an emulsion is obtained;
    heating the emulsion until the carrier is melted; and
    cooling the emulsion, thus the sustained-release composition is obtained.

12. The method of claim 11, wherein the paraffin wax of the carrier is represented by the formula (I):

$$C_m H_{2m+2} \qquad (I),$$

wherein m is 20 to 34.

13. The method of claim 11, wherein the second solution comprises a water, a surfactant and a thickening agent.

14. The method of claim 6, wherein the first solution and the carrier are contained in a weight ratio of 3:1 to 8:1.

15. A method for treating chronic wounds, comprising:
administering an effective amount of the sustained-release composition of claim 1 to a subject suffering from the chronic wounds.

* * * * *